United States Patent
Hanson et al.

(10) Patent No.: US 7,012,203 B2
(45) Date of Patent: Mar. 14, 2006

(54) FOOT SWITCH PEDAL CONTROLLER FOR A SURGICAL INSTRUMENT

(75) Inventors: Michael R. Hanson, Atascadero, CA (US); Richard G. Thorlakson, San Luis Obispo, CA (US); B. J. Barwick, Jr., Shell Beach, CA (US)

(73) Assignee: Carl Zeiss Surgical GmbH, Oberkochen (DE)

( * ) Notice: Subject to any disclaimer, the term of this patent is extended or adjusted under 35 U.S.C. 154(b) by 696 days.

(21) Appl. No.: 09/949,123

(22) Filed: Sep. 7, 2001

(65) Prior Publication Data

US 2003/0047434 A1 Mar. 13, 2003

(51) Int. Cl.
 *H01H 3/14* (2006.01)

(52) U.S. Cl. .................. 200/86.5; 74/512; 433/101

(58) Field of Classification Search ........... 74/560–562, 74/512; 200/61.89, 86.5; 307/119; 338/2, 338/108, 153; 433/101, 113
See application file for complete search history.

(56) References Cited

U.S. PATENT DOCUMENTS

| | | | |
|---|---|---|---|
| 3,693,613 A | 9/1972 | Kelman | |
| 3,983,344 A | * 9/1976 | Straihammer | 200/86.5 |
| 4,168,707 A | 9/1979 | Douvas et al. | |
| 4,200,025 A | 4/1980 | Currier | |
| 4,293,746 A | 10/1981 | Braaten | |
| 4,523,911 A | * 6/1985 | Braetsch et al. | 433/101 |
| 4,837,857 A | 6/1989 | Scheller et al. | |
| 4,933,843 A | 6/1990 | Scheller et al. | |
| 4,970,486 A | 11/1990 | Gray et al. | |
| 4,983,901 A | 1/1991 | Lehmer | |
| 5,044,478 A | 9/1991 | Kaesgen et al. | |
| 5,177,473 A | 1/1993 | Drysdale | |
| 5,242,404 A | 9/1993 | Conley et al. | |
| 5,268,624 A | 12/1993 | Zanger | |
| 5,317,981 A | 6/1994 | Hashiride et al. | |
| 5,322,084 A | 6/1994 | Ghiassian | |
| 5,342,293 A | 8/1994 | Zanger | |
| 5,422,521 A | 6/1995 | Neer et al. | |
| 5,423,231 A | 6/1995 | Helfrich et al. | |
| 5,554,894 A | * 9/1996 | Sepielli | 307/119 |
| 5,580,347 A | 12/1996 | Reimels | |
| 5,635,777 A | 6/1997 | Telymonde et al. | |
| 5,733,256 A | 3/1998 | Costin | |
| 5,766,146 A | 6/1998 | Barwick, Jr. | |
| 5,787,760 A | 8/1998 | Thorlakson | |
| 5,968,007 A | 10/1999 | Simon et al. | |
| 5,983,749 A | 11/1999 | Holtorf | |
| 6,360,630 B1 | * 3/2002 | Holtorf | 74/512 |

FOREIGN PATENT DOCUMENTS

| | | |
|---|---|---|
| EP | 0 085 518 | 8/1983 |
| WO | WO 92/20310 | 11/1992 |

* cited by examiner

*Primary Examiner*—Michael A. Friedhofer
(74) *Attorney, Agent, or Firm*—Squire, Sanders & Dempsey L.L.P.

(57) ABSTRACT

A foot operable controller for a surgical instrument having a main foot pedal assembly providing either proportional or linear control signals when moved laterally and in a vertical direction. Friction between an operator's foot and the foot pedal is minimized by a foot pad having a rotating heel plate. A neutral zone between left and right control positions of the foot pedal enables the operator to move his foot freely without changing control settings. Vertical displacement of the foot pedal is indicated by a plurality of mechanical detents during both upward and downward travel. Changing detent resistance alerts the operator to the vertical position of the foot pedal, indicating that further vertical displacement will change an instrument control signal corresponding to the new foot pedal position, thus providing sensory feedback to the operator indicating a change in the functional mode when the foot pedal is moved.

54 Claims, 11 Drawing Sheets

FOOT SWITCH PEDAL CONTROLLER FOR A SURGICAL INSTRUMENT

BACKGROUND OF THE INVENTION

1. Field of the Invention

A foot operable controller for a surgical instrument and, more particularly a, foot operable controller for an ophthalmic surgical instrument

2. Prior Art

Foot operable devices for controlling surgical instruments are well known and represented in the art. In the treatment of cataracts, a phacoemulsification instrument is widely used for the fragmentation and removal of a crystalline lens prior to replacing the defective lens with an artificial lens. Such an apparatus requires the administration of a preferred level of ultrasonic energy to the lens and the introduction of an irrigation fluid stream to the operative site and the removal of fragmented tissue from the operative site via an aspiration vacuum. Accordingly, in order to free the surgeon's hands, control signals are supplied to the instrument via a foot operable controller. The foot operable controller includes independent means for generating both proportional and/or fixed control signals for establishing the desired ultrasonic power level, irrigation fluid flow and varying the aspiration vacuum pump in response to foot movement.

Various systems have been used to control surgical instruments in general, and phacoemulsification equipment in particular. For example, one approach used a foot-operated controller to control a surgical instrument wherein azimuthal rotation of an operator's foot selects a function from a menu. After the function is selected, the foot-pedal is returned to a center position and depressed (or elevationally moved) to generate a control signal for the selected function. The rotational azimuthal movement of the pedal does not provide a displacement-proportional control signal and the foot pedal could not be rotated and depressed at the same time.

Another approach to providing control signals using a foot activated controller utilizes a digital electronic foot operable controller comprising a rotatable shaft affixed to a foot pedal. The shaft includes a shaft encoder, which provides a digital signal related to the rotational status of the shaft. The output signal from the shaft position encoder is input to a control card, which uses the signal to control various functions of the medical apparatus.

Yet another system employing a foot pedal controller has a rotatable arm having three spaced conductors on a surface thereof. The arm rotates over regions bearing spaced pairs of electrodes; each pair of spaced electrodes corresponding to a different function. Thus, rotation of the foot pedal can be used to turn on the flow of irrigating fluid to an irrigating channel in a phacoemulsifier hand piece, apply a vacuum to an aspiration channel in the hand piece and deliver ultrasonic power to the hand piece. Another example uses a dual position foot pedal control unit that includes a base and a pedal arrangement that enables a user to generate control signals using his/her toe and sole. Switching between the dual positions is accomplished by rotation of the foot-pedal. The controller enables a user to switch between two different functions by rotating the foot to generate a control signal for the function by either sliding the foot pedal with respect to the base or depressing the foot-pedal.

Foot control devices have also been used to control other types of instruments. For example, one foot controlled device was used to generate control signals for a zoom microscope. Vertical movement of the foot pedal brings the image into focus while rotation of the foot pedal changes the magnification in a displacement-proportional manner. In addition, the foot pedal may be moved reciprocally in a plane parallel to the azimuthal plane and orthogonal to the direction of vertical motion to change the field of view.

In a phacoemulsification system, aspiration vacuum developed by the system is modulated by a foot operable controller to increase or decrease suction at the tip of the operating instrument from zero to a desired level. Additionally, the foot operable controller may also be switchable between a fragmentation mode which is used to control the phacoemulsification module and hand piece and a cutter mode which is used to control operation of a micro surgical cutting instrument. When the selector is set to fragmentation, and the infusion mode of the infusion/aspiration module is set on auto, depressing the foot pedal to a first position, signaled by an audible click, activates infusion to the handpiece. Depressing the foot pedal to a second position, signaled by a second click, activates both infusion and aspiration. Depressing the foot pedal to a third position activates infusion, aspiration, and phacoemulsification.

During phacoemulsification, the surgeon is concentrating on performing microscopic movements of the phacoemulsification probe within the eye. Such movements are guided by the surgeon by viewing the eye through a high power surgical microscope. Typically, the surgeon will not want to disengage his view from the microscope to look at the panel of the instrument to determine what mode the instrument is in, or what power levels or aspiration levels are being used. For this reason, various attempts have been made to provide a foot operable controller that provides some form of sensory feedback to the surgeon so that he or she may determine the mode and settings of the machine while maintaining their view through the surgical microscope.

One attempt at providing feedback to the surgeon using a foot operable controller provides a plurality of resistance forces which are staged to provide increasing resistance at predetermined points along the rotational travel of the foot pedal. Thus, the foot pedal provides different tactile feedback for each of the different ranges of operation. Foot pedals utilizing this method of providing feedback typically provide two or more resistance ranges as the foot pedal is depressed. Typically, foot pedals of this type provide for increasing ranges of resistance, such as may be achieved by utilizing one spring for the first range, and then another spring, which may or may not be a stronger spring, for the next range and so forth. However, such systems usually provide no warning that the next range is about to be entered, thus small adjustments in pressure on the foot pedal may cause unwanted changes in the function or power level of the phacoemulsifier.

There remains a need for a foot operable instrument control device which includes means for alerting the operator that further movement of the foot in the up/down or side to side direction will result in the change of a control signal to the instrument. Such a warning alert enables the operator to move his/her foot freely over certain ranges of motion without being concerned about changing the signal. When the surgeon is ready, the foot is moved to a position where a tactile response alerts the operator that further foot movement will change an instrument control signal. This tactile response needs to provide an equally strong alert to the operator both during foot pedal depression and elevation.

SUMMARY OF THE INVENTION

The invention provides for improved systems and methods of controlling a surgical instrument using a foot operable controller that provides control signals for activating and controlling various functions of the surgical instrument. The foot operable controller includes a foot pedal configured to provide vertical movement perpendicular to the base of the controller as well as lateral movement in a plane substantially parallel to the base of the controller. When the foot pedal is depressed to move the foot pedal in the vertical direction, a detent mechanism provides tactile signals to indicate when the foot pedal is approaching a place in its range of vertical movement that will cause a different function to be activated.

In one embodiment of the invention, a foot pedal assembly is mounted to a base in such a manner that the foot pedal assembly may move upwardly and downwardly in the vertical direction. A detent mechanism comprising a disengageable cam and cam follower provide resistance to vertical movement of the foot pedal, such that as the foot pedal is depressed, the amount of resistance decreases as the foot pedal approaches a transition zone between different control segments of the foot pedal's vertical range of movement. As the transition zone is traversed by further depression of the foot pedal, the resistance again increases. The process occurs in reverse when downward pressure on the foot pedal is relaxed, allowing the foot pedal to move in an upward direction and providing tactile feedback to the surgeon that transition zones are being entered and that functions of the instrument are about to be changed.

In another embodiment of the invention, the foot pedal controller includes a foot pedal assembly mounted to abase, and including a foot pedal having a slidable foot pedal cover that is configured to move laterally with respect to a foot pedal base. The slidable foot pedal cover is operably connected to a signal generator that is responsive to lateral movement of the foot pedal cover to provide control signals to a surgical instrument. The control signals provided may be linear or proportional.

In a further embodiment of the invention, the foot pedal controller includes a foot pad pivotally mounted to a base of the foot pedal controller and having a portion overlying the slidable foot pedal cover. The foot pad may be manufactured from a low friction material to provide substantially frictionless motion of the foot pad over the foot pedal cover. A top surface of the foot pad may be covered in a friction-forming material so that when a surgeon places his or her foot upon the foot pad, the surgeon may move his or her foot laterally and the foot pad will move with the surgeons foot movement. The foot pedal cover includes right and left resistance means, for example, spring loaded push plates, mounted on the right and left sides of the slidable foot pedal cover, and the foot pad is disposed between the right and left resistance means. The width of the foot pad is less than the spacing between the right and left resistance means so that the foot pad may be laterally translated through a neutral zone before a right or left edge of the foot pad encounters the right or left resistance means.

In an alternate embodiment, the foot pedal includes foot pad having a slot through which extends a post in mechanical communication with the signal generator. In this embodiment, the foot pad may be moved about the post without engaging the signal generator unless the foot pad is moved sufficiently in one direction such that a lateral end of the slot engages the post, communicating further movement in that direction to the signal generator, which generates a control signal in response thereto. In this manner, various embodiments of the present invention provide a foot pad that allows for movement of the surgeons foot through a selected distance without engaging the signal generator, thus preventing activation of any switches or causing an changes to the functions of the surgical instrument.

In another embodiment, the foot pad includes a plurality of mounting holes configured to be captured by a rotatable heel plate pivotally mounted on the controller base, thus allowing the foot pad to be adjusted to accommodate various size feet.

Other features and advantages of the present invention will become more apparent from the following detailed description, taken in conjunction with the accompanying drawings, which illustrate, by way of example, the principles of the invention.

DESCRIPTION OF THE PREFERRED EMBODIMENTS

Figure 1:
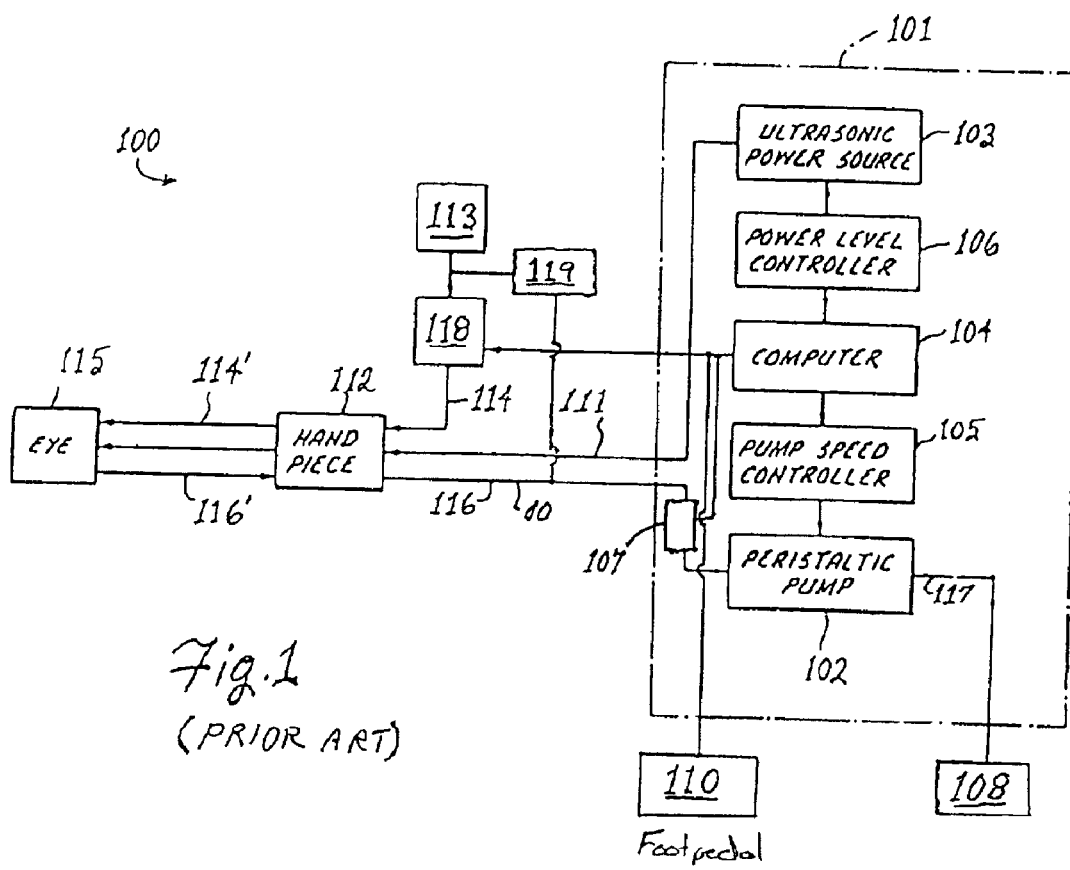
FIG. 1 is a block diagram of an ultrasonic surgical apparatus wherein the apparatus' control parameters are established by means of a programmable controller and a foot operable controller.

The foot operable controller of the present invention is versatile and may be used to control a variety of surgical apparatus. It is particularly adapted to control ophthalmic surgical instruments such as instruments employed for phacoemulsification, vitrectomy, and diathermy procedures. Accordingly, it is instructive to discuss the functional control elements present in phacoemulsification instruments with which the foot operable controller may be advantageously used. With reference now to FIG. 1, a phacoemulsification apparatus 100 is illustrated in block diagrammatic form. The apparatus 100 has a control unit 101, indicated by the broken line in FIG. 1, which includes a variable speed peristaltic pump 102, which provides a vacuum source, a source of pulsed ultrasonic power 103, and a microprocessor-based programmable computer 104 that provides control outputs to pump speed controller 105 and ultrasonic power level controller 106.

A vacuum sensor 107 provides an input to computer 104 establishing the vacuum level on the input side of a peristaltic pump 102. Suitable venting may be provided by reversing the peristaltic pump 102. A foot pedal 110 is provided to enable a physician to control irrigation fluid flow, aspiration rate, and ultrasonic power level as will be hereinafter described.

The control unit 101 supplies ultrasonic power on line 111 to a phacoemulsification hand piece 112. An irrigation fluid source 113 is fluidly coupled to hand piece 112 through line 114 and from the handpiece to the eye through irrigation line 114'. The flow rate of the irrigating fluid contained in fluid source 113 through the hand piece is driven by gravity and is usually adjusted by raising and lowering the fluid source with respect to the hand piece and is turned on and off by valve 118. The irrigation fluid and ultrasonic power are applied by handpiece 112 to a patient's eye 115. Aspiration of irrigating fluid and fragmented lens tissue from the eye is achieved by means of a peristaltic pump 102 housed within the control unit 101 through aspiration lines 116 and 116'. A programmable computer 104 responds to actual vacuum levels in the input line 116 by measuring the signal from the previously mentioned vacuum sensor 107 and then controlling the flow rate of the peristaltic pump 102.

If the hand piece aspiration line 116' becomes occluded, the vacuum level sensed by vacuum sensor 107 will increase. The computer 104 preferably includes operator-settable limits for aspiration rate, vacuum level and the level of ultrasonic power delivered to the hand piece and hence the eye. When the vacuum level sensed by vacuum sensor 107 reaches a predetermined level as a result of occlusion of the hand piece aspiration line 116', programmable computer 104 instructs pump speed controller 105 to change the speed of the peristaltic pump 102 which, in turn, changes the aspiration rate.

In the event that aspirated material occludes the aspiration line, the speed of the peristaltic pump 102 can either be increased or decreased (or the level of ultrasonic power varied) to either reestablish patency of the aspiration line or to hold the material in contact with the handpiece. When the occluding material is broken up or otherwise removed, the vacuum sensor 107 registers a drop in vacuum level causing the programmable computer 104 to change the speed of peristaltic pump 102 to an unoccluded operating speed. Alternatively, or additionally, the irrigation fluid source 113 may further provide a reflux fluid supply to the aspiration line 116' by switching the flow of irrigation fluid to the aspiration line 116 thru controlling valve 119. The reverse flow (reflux) of irrigation fluid through the aspiration line 116 and 116' and the aspiration channel within the hand piece may be used to remove such an obstruction.

While many of the control settings for such an instrument can be established by means of preoperatively programmed instructions, various intraoperative procedures require the instantaneous change in one or more control settings. The ultrasonically mediated emulsification of a lens and aspiration thereof from the eye is a complex procedure that requires the delicate balancing of powerful forces. Precise intraoperative control of such forces is essential and is facilitated by means of a programmable foot operable controller in accordance with the present invention.

Figure 2:
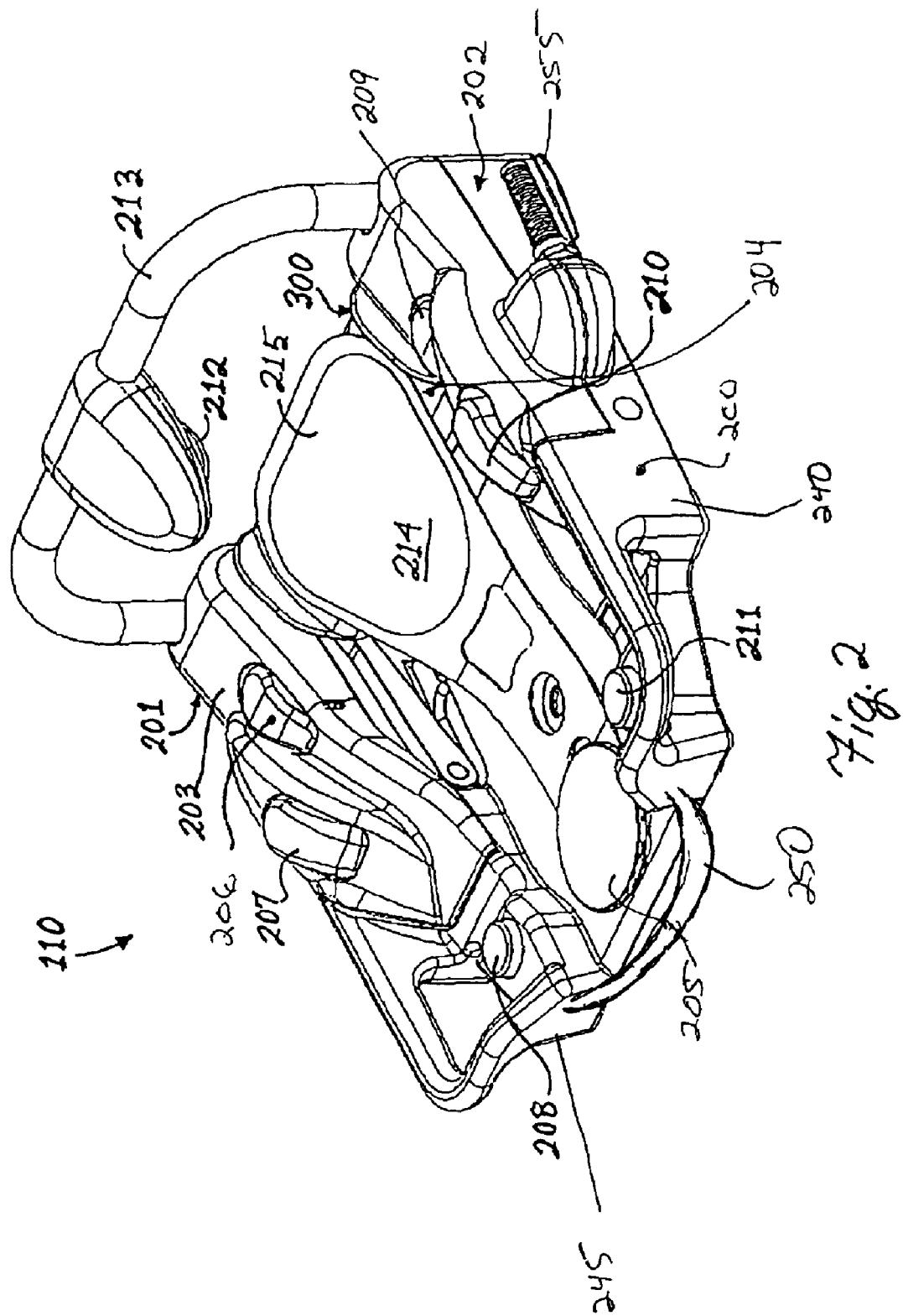
FIG. 2 is a perspective isometric view of a foot operable controller for a surgical apparatus in accordance with the present invention.

With reference now to FIG. 2, the foot operable controller 110 has a base 200 (visible in FIGS. 3 and 4), a left side 201, a right side 202, and a cover 203 overlying the base 200. A foot pedal assembly 300 is pivotally attached to the base 200. A heel plate 205 having a shaft mounted on an underside of the heel plate 205 is rotatably mounted on base 200 by mounting the shaft in a hole formed in a top surface of base 200 located adjacent a proximal end of base 200. A foot pad 214 has a proximal end portion having a series of holes located therein and sized to receive the shaft of heel plate 205. The hole in base 200 for receiving the shaft of heel plate 205 is formed to a depth sufficient to maintain a space between the top surface of base 200 and the underside of heel plate 205 when the shaft is fulling inserted into the hole such that the proximal end of the foot pad 214 may freely pivot about the shaft of heel plate 205. The foot pad 214 has a distal end 215 that overlies the foot pedal 204.

Cover 203 has a distal end and a proximal end corresponding to the proximal and distal ends of base 200. Cover 203 also has a right side 240 and a left side 245. A toe catch 250 is mounted on the proximal end of cover 203 between right side 240 and left side 245. Toe catch 250 is mounted such that there a space is created between a bottom surface of toe catch 250 and a surface upon which base 200 is located so that the toe of a shoe can fit into the space, allowing an operator lift the proximal end of the foot operable controller 110 with the operator's foot, thus providing leverage to move the base 200 about the surface to adjust the location of the foot operable controller 110 as desired by the operator. To facilitate moving the foot operable controller 110, a low friction material 255 such as Teflon, a product of Du Pont, Inc., nylon or other suitable material may be mounted on the bottom surface of base 200. Preferably, such low friction material 255 is mounted on only a distal portion of base 200 so that when base 200 is lying in a substantially flat position on a surface, the foot operable controller 110 is suitably stable and tends to remain in place when the foot pedal is operated. Alternatively, low friction material 255 may be replaced with some other means, such as wheels, rollers or the like, of providing ease of movement when the proximal end of the foot operable controller 110 is lifted using toe catch 250.

The foot operable controller 110 further includes six foot-activatable switches 206–211. Three of the switches 206, 207 and 208, are disposed on the left side 201 of the controller 110 and are foot-accessible. Three additional foot-accessible switches 209, 210 and 211 are disposed on the right side 202 of the foot operable controller 110. A seventh toe-activatable non-linear switch 212 is disposed on a yoke 213 attached to the cover 203. Each switch 206–212 is programmable and may be selected by the surgeon to activate a particular preprogrammed control setting in an "on/off" (non-linear) manner in accordance with the particular surgeon's preference. In addition, the lateral displacement of the foot pedal assembly 300 may be used in order to select and control a particular control parameter in either a linear or non-linear manner; the choice of control parameter depending on the surgeon's preprogrammed instructions. The heel plate 205 facilitates selection of the foot-activatable switches 206–211 in that the heel plate 205 allows an operator to move his or her foot to the side and activate foot-activatable switches 206–211 without moving the foot pedal laterally.

Movement of the foot pedal assembly 300 provides either a linear or non-linear displacement-proportional signal output in response to both vertical and lateral or azimuthal motion. As stated earlier, the variable parameter controlled by the position of the foot switch will depend upon the selection of the particular switch settings on the control unit 101 programmed by the operating surgeon. For example, when the control unit 101 is programmed to operate in the phacoemulsification mode, as the foot pedal assembly 300 is depressed, the signal output from the vertical displacement of the foot pedal may sequentially control the flow irrigation fluid to the eye, the aspiration rate of fluid from the eye and finally the ultrasonic power applied to the handpiece.

Figure 3:
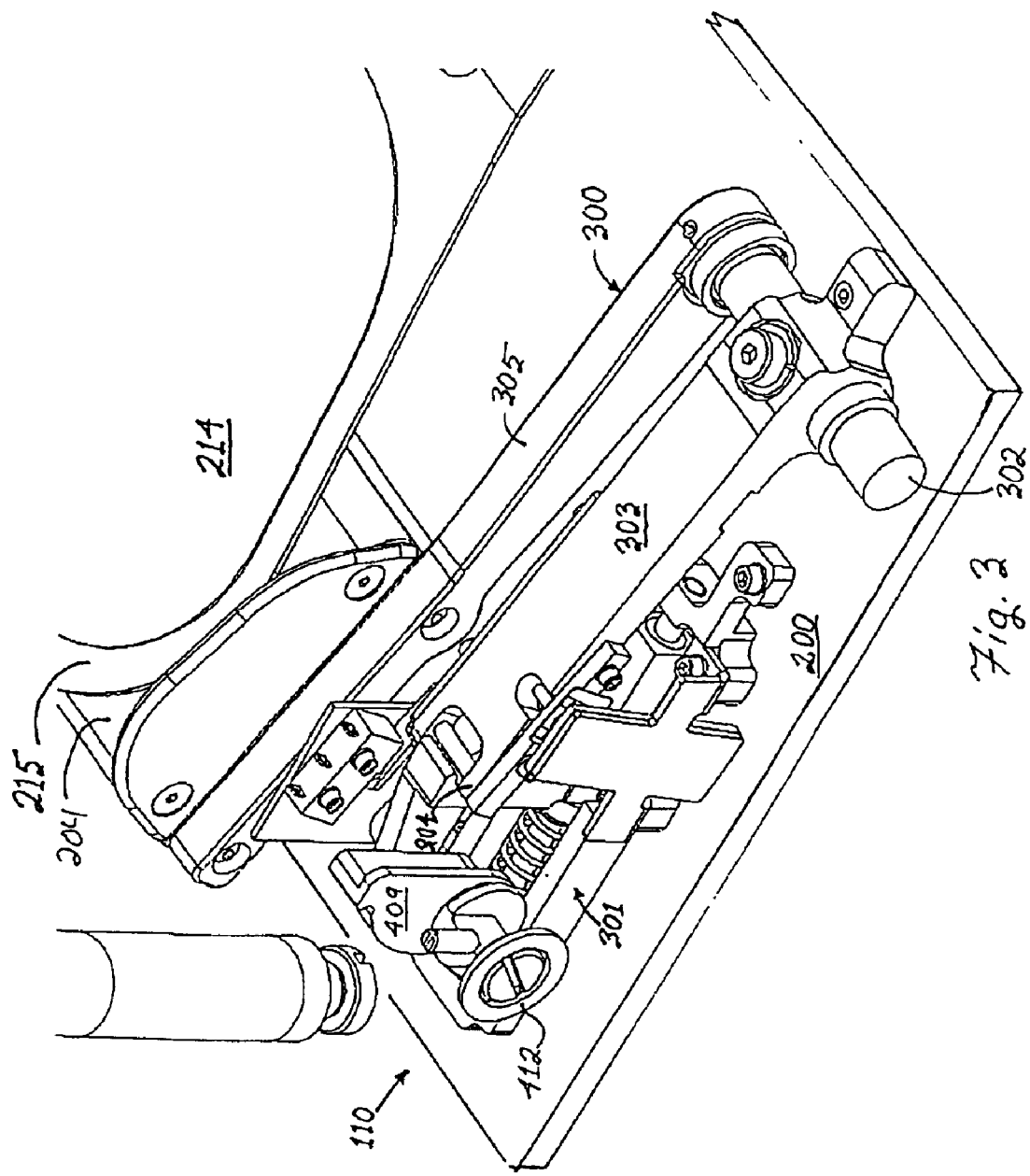
FIG. 3 is a top left perspective view of the foot operable controller of FIG. 2 with the cover removed to expose a portion of the foot pedal assembly connected to a detent mechanism for indicating the vertical displacement of the foot pedal assembly.
Figure 4:
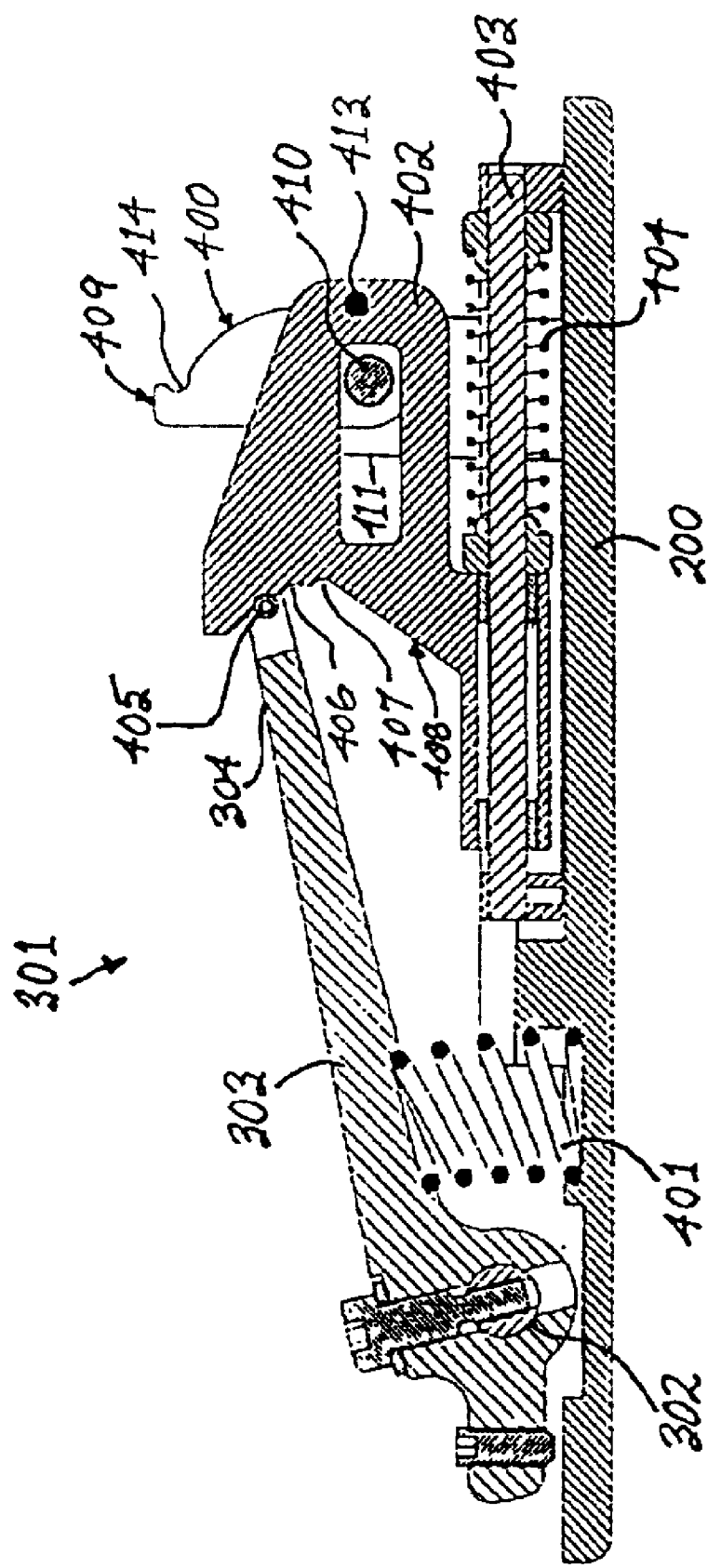
FIG. 4 is a cross-sectional side view of a preferred embodiment of the detent mechanism for use with a vertical displacement foot pedal assembly in accordance with the present invention.

FIG. 3 is a left perspective view of the foot operable controller 110 with the cover 203 removed illustrating the structural relationship between the foot pedal assembly and a detent assembly 301. Depression of the foot pedal 204 on the foot pedal assembly 300 is capable of operating a plurality of sequential functions. Accordingly, it is desirable that the surgeon be able to recognize the point at which further depression of the foot pedal will activate a new function and/or further release will deactivate the function. In a noisy environment where equipment and people are carrying out their respective duties, an audible signal such as a click may or may not be heard, and thus the surgeon may not receive adequate feedback to determine which function has been actuated or de-actuated.

In order to alert the surgeon to the imminent activation of a new function, the foot pedal assembly 300 has been coupled to a detent assembly 301 to provide the surgeon with exact elevational information regarding the vertical displacement of the foot pedal 204. The foot pedal assembly 300 includes the foot pedal 204 and parallel foot pedal support arms 305 and 305' (support arm 305' not visible in FIGS. 3 and 4). Support arm 305 is rigidly attached to a rotatably mounted shaft 302. Shaft 302, in turn, is attached to the detent arm 303, which is part of the detent assembly 301. When the foot pedal 204 is depressed, shaft 302 rotates, thereby depressing the distal end 304 of the detent arm 303. This is illustrated in greater detail in FIG. 4 wherein the detent assembly 301 of the present invention is shown in side cross-sectional view.

The detent assembly 301 includes a main pedal return spring 401 affixed to the base 200. Spring 401 is disposed between the base and the detent arm 303 to bias the detent arm 303 in an upward direction. A cam carriage 402 is slidably mounted on a rail 403, which rail is rigidly attached to base 200. The cam carriage 402 is urged towards the distal end 304 of the detent arm 303 by means of a carriage return spring 404. A cam follower 405 is rotatably attached to the distal end 304 of the detent arm 303 and moves against the cam carriage 402 when the detent arm 303 is depressed or elevated in response to rotation of shaft 302. As the foot pedal 204 (not shown in FIG. 4) is depressed, rotation of shaft 302 forces the cam follower 405 downwardly. As the cam follower proceeds in its downward trajectory in response to foot pressure on the foot pedal 204, the carriage return spring 404 is compressed and the cam follower encounters a succession of detents, two of which are shown at 406 and 407. While only two detents are shown, it will be obvious to those skilled in the art that more than two detents may be provided as needed for control of various desired functions.

Each detent provides a change in the mechanical resistance that opposes depression motion of the foot pedal 204 on the foot pedal assembly 300. For example, as the foot pedal 204 is depressed by a surgeon, the change in resistance alerts the surgeon that further movement of the foot pedal will cause a transition between intraoperative instrument functions. A further change in resistance may also be caused by the interaction between the cam follower 405 and the detent to indicate when a change to a particular operative signal from the foot controller has occurred. The detent assembly 301 operates similarly when the foot pedal 204 is elevated from a depressed position, providing the operator with a resistance signal that indicates that further movement of the foot switch will cause a transition between intraoperative instrument functions and when a change to a particular operative signal from the foot controller has occurred.

The portion of the cam carriage 402 that maintains mechanical contact with cam follower 405 disposed on the distal end 304 of detent arm 303 throughout the range of vertical motion of the foot pedal 204 has a curvilinear edge defining a cam profile 408. The cam profile 408 may be removed by means of a cam profile selector 409 that is rotatably mounted to base 200 by means of profile selector shaft 410 and shaft mount 411. The cam profile selector 409 provides means for disengaging the cam follower 405 connected to the distal end of the detent arm 303 from contact with the cam profile 408 of the cam carriage 402. When the cam profile selector 409 is manually rotated 90 degrees in a clockwise direction by a cam profile selector switch 412 (shown in FIG. 3), a second cam profile 400 urges a second cam follower 413 on the cam carriage rearwardly until the second cam follower 413 mainly engages a detent 414 and locks the cam carriage 402 in a retracted position (i.e., with the carriage return spring 404 compressed), thereby disengaging the cam follower 405 from pressing against the cam profile 408 edge of the cam carriage 402. When the cam profile selector 409 is activated and the cam follower 405 disengaged from cam profile 408, depression and/or elevation of the foot pedal provides a smooth, continuous tactile impression over the allowable vertical range of foot pedal motion.

Figure 5:
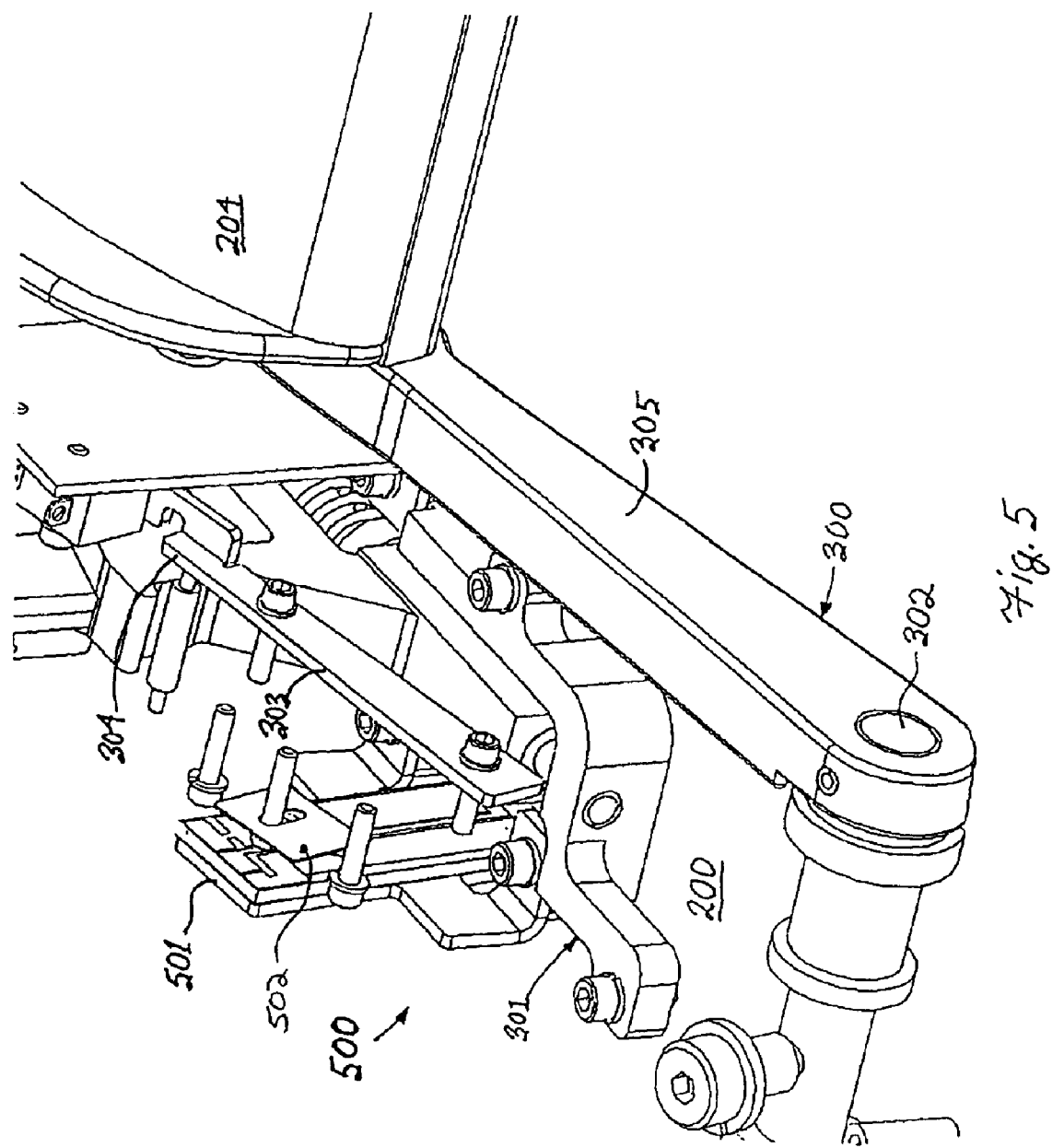
FIG. 5 is a top right perspective view of the left side of the foot operable controller of FIG. 2 with the cover removed to expose a portion of the foot pedal assembly connected to a detent mechanism for indicating the vertical displacement of the foot pedal assembly.

With reference to FIG. 5, the modified foot pedal assembly 300 includes a foot pedal 204 in combination with the detent assembly 301 in accordance with the present invention. The detent assembly 301 includes a linear potentiometer 501 rigidly mounted on base 200. The potentiometer 501 interacts with an electrically conductive slidable brush 502 attached to the detent arm 303. As the foot pedal 204 is depressed, the brush 502 moves in response to the repositioning of the detent arm 303 and provides a displacement-proportional control signal to the surgical instrument.

In summary, the foot operable controller 110 in accordance with the present invention, useful for enabling a surgeon to control a surgical instrument, includes a floor-supportable controller base having a lower surface and an upper surface. The controller 110 includes a foot pedal assembly 300 comprising a foot pedal 204 affixed to a shaft 302 that is rotatably mounted on the upper surface of the controller base 200. A detent assembly 301 is mounted on the upper surface of the controller base and is responsive to rotation of the shaft 302. The detent assembly provides means for exerting a desired change in resistance to rotation of the shaft when the shaft is in a predetermined rotational position. The foot operable controller preferably further comprises a control signal generating device such as, for example, a linear potentiometer 501 or a shaft position encoder, wherein the control signal generated by the control signal generator has a measurable variable property associated therewith, such as electrical resistance or voltage. The value of the variable property comprises the control signal and varies in response to rotation of the shaft. Upon movement of the foot pedal by the surgeon, the shaft rotates thereby generating a control signal, which is communicated to the instrument to control the operation thereof.

Figure 11:
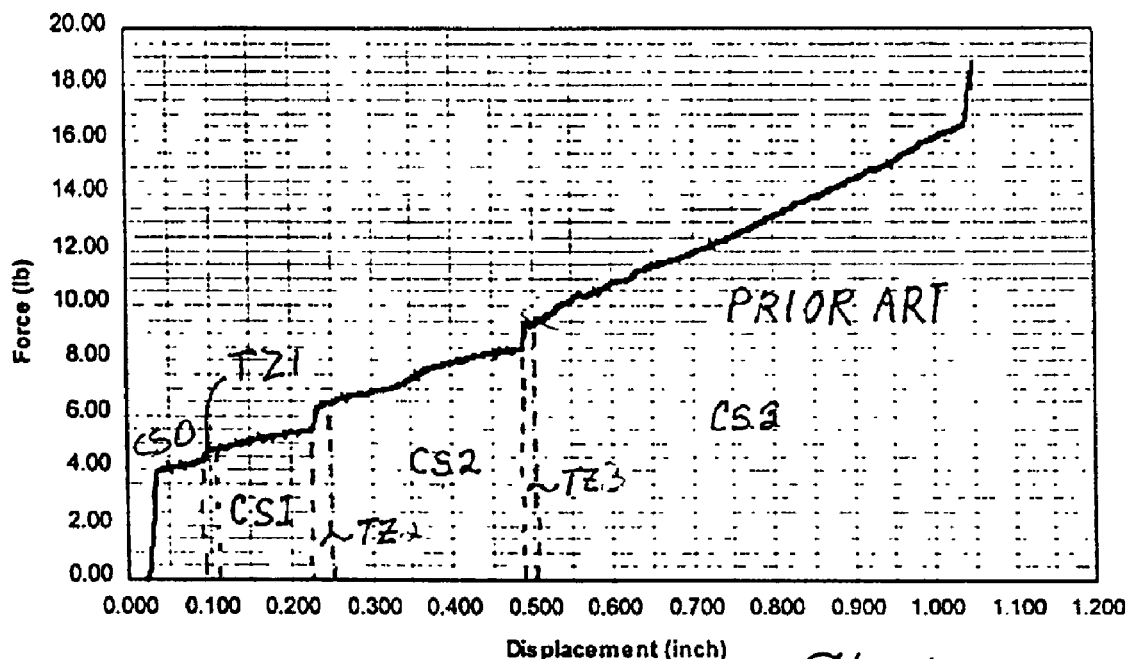
FIG. 11 is a graph showing the progressively increasing force required to move a representative prior art foot pedal through its downward vertical travel distance.
Figure 12:
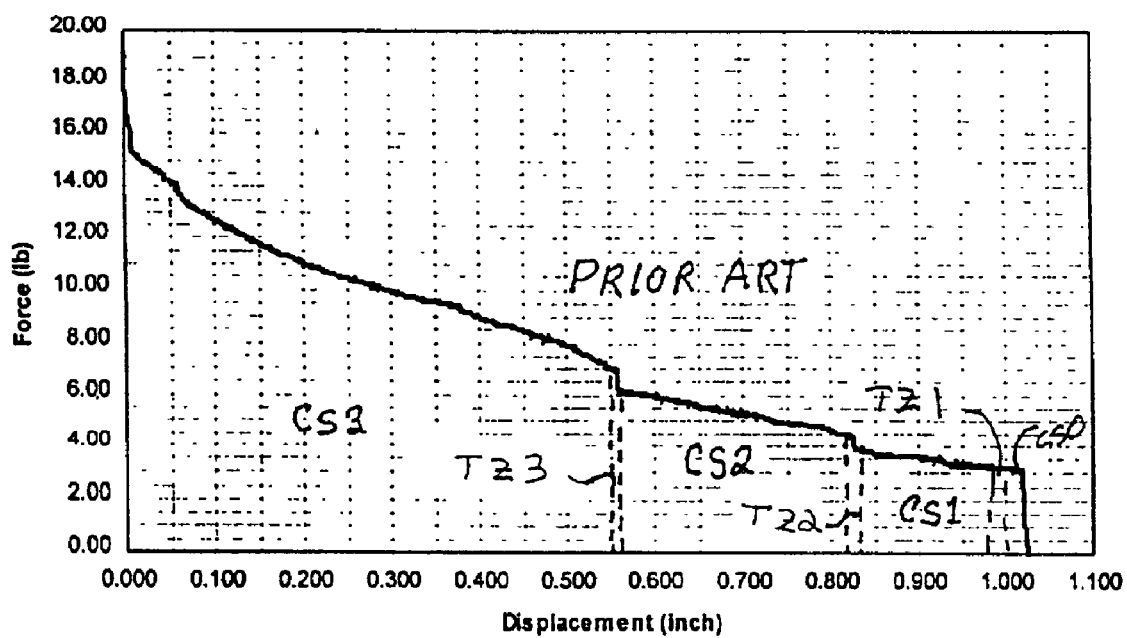
FIG. 12 is a graph showing the progressively decreasing force required to move a representative prior art foot pedal through its upward vertical travel distance when the foot pedal is initially fully depressed.
Figure 13:
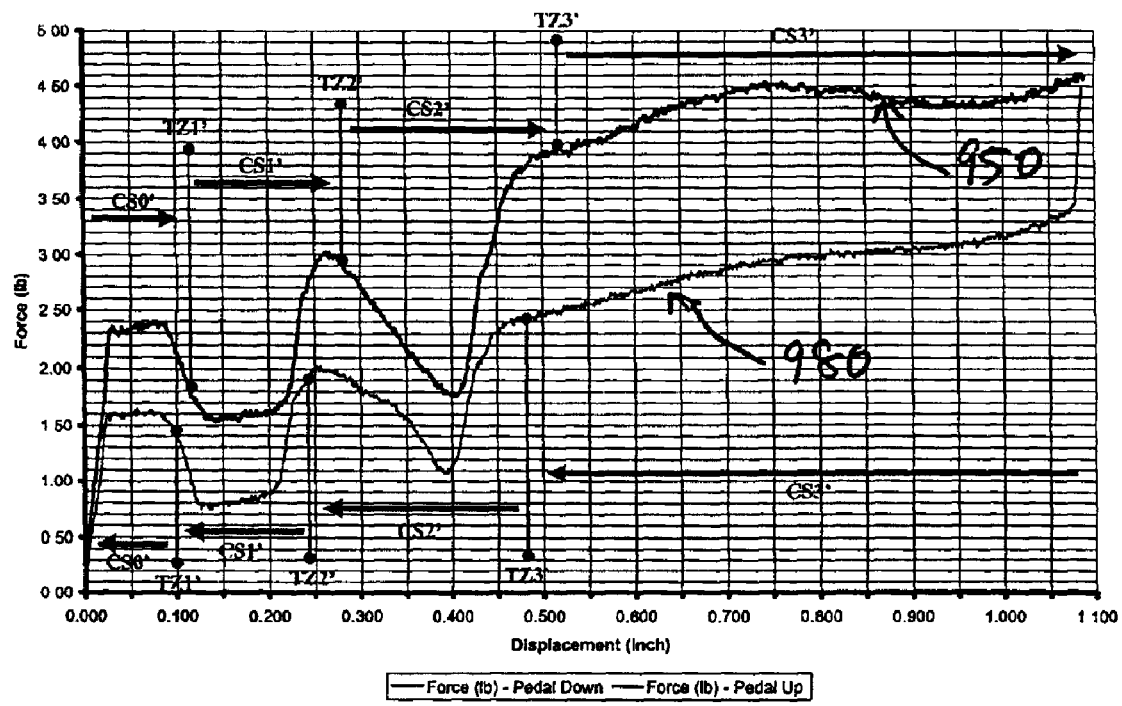
FIG. 13 is a graph illustrating the applied force required to move a foot pedal upwardly and downwardly through its vertical travel in accordance with the present invention.

The tactile effect provided by the detent assembly of the present invention is different from prior art foot operable controllers as is illustrated in FIGS. 11–13. With reference to FIGS. 11 and 12, when a foot pedal in accordance with the prior art is depressed (FIG. 11), the force applied to the foot pedal to effect displacement of the foot pedal in a downward direction progressively increases in the manner illustrated in FIG. 11. When the force on the foot pedal is relaxed to elevate the foot pedal of FIG. 11 back to its fully upright position, as shown in FIG. 12, the force applied to the foot pedal is progressively decreased in a manner substantially mirroring the force/displacement curve of FIG. 11. It should be understood that the example illustrated in FIGS. 11 and 12 is for a single prior art foot operable controller, and offered for illustrative purposes only. Prior art foot operable controllers exhibit foot pedal force/displacement characteristics wherein the slope of the force vs pedal displacement curve is positive when the pedal is depressed, as shown in FIG. 11, and is negative in the upward travel direction as seen in FIG. 12. In particular, when the foot pedal is initially depressed beyond the off position CS0, through transition zone TZ0, and displaced into the region corresponding to a first control signal CS1, a first control signal is conducted to a surgical instrument. When the foot pedal passes through a second transition zone, at TZ1, the foot pedal enters a second region CS2 wherein a second control signal is generated and conducted to the surgical instrument. The magnitude of such control signals may either be constant or have a value that is proportional to the foot pedal position.

FIG. 13 illustrates the variable resistance provided to foot pedal depression provided by the present invention. As illustrated by line 950, when the surgeon begins applying downward pressure on the foot pedal, the resistance to downward depression increases as the foot pedal traverses a control signal region CS0'. At a point in the traverse of region CS0', the resistance provided by the detent mechanism may flatten out, indicating to the surgeon that a change in control function, or transition zone, is being approached. Depending on how the surgical instrument controlled by the foot pedal is programmed, further depression of the foot pedal may provide either linear or proportional control of some other function of the instrument.

Unlike the exemplary force vs displacement curve for the representative prior art foot operable controller shown in FIGS. 11 and 12, further depression of the foot pedal of the present invention causes the foot pedal to approach a transition region TZ1'. As the depression of the foot pedal cause the foot pedal to enter transition TZ1', the detent mechanism causes the resistance to further depression of the foot pedal to decrease, providing a tactile signal to the surgeon that the foot pedal has been depressed far enough to enter a transition zone. As the transition zone is traversed by further depressing the foot pedal, the detent mechanism may increase the resistance to further depression signaling that a further control region is about to be entered. Since each further control signal region, for example, control regions CS2' and CS3', are preceded by transition zones, the surgeon knows, from the tactile feedback caused by the reduction of resistance to further depression, indicating that a control region has been exited, and then an increase of resistance, that further depression of the foot pedal will cause the foot pedal to enter a different control region, activating a different function of the instrument.

In summary, the resistance applied by the detent mechanism of the present invention, depicted as the force necessary to further depress a foot pedal as function of foot pedal displacement in line 950 of FIG. 13, decreases as the foot pedal exits a control signal region such as CS0' and enters a transition zone such as TZ1', reaches a minimum and then increases as the foot pedal enters the next control signal region, such as CS1'. The resistance may increase still further as the foot pedal traverses the control signal region and enters an adjacent transition zone, such as TZ2'.

Starting from the fully depressed position, as the foot pedal force is relaxed, as shown by line 980 of FIG. 13, a similar sensation is perceived by the surgeon as the foot pedal exits control signal region CS3' and traverses control signal regions CS2', CS1' and CS0' respectively. For example, as the surgeon reduces the downward force applied to the foot pedal, the detent mechanism causes the resistance to downward pressure to decrease as the foot pedal leaves control region CS3' and enters transition zone TZ3'. It should be noted that this decrease in resistance is felt by the surgeon as a rapid decrease in the force needed to maintain the foot pedal in a static position. As the surgeon further relaxes the downward force applied to the foot pedal, the foot pedal continues to rise, and the resistance applied by the detent mechanism also increases, indicating to the surgeon that the foot pedal is approaching another control region, in this example, control region CS2'. Further reduction of downward force will result in further upward movement of the foot pedal, resulting in entering transition zone TZ2', which will be indicated by a rapid decrease in resistance, followed by an increase in resistance signaling the approach, and entry into, of control region CS1'. A similar change is resistance will be perceived as the foot pedal is relaxed still further, traversing transition zone TZ1' and entering control region CS0'.

The tactile sensation perceived by the operator of the foot operable controller of the present invention as the foot pedal traverses its range of motion, particularly in the upward direction, is more informative than the tactile sensation perceived by the operator with prior art controllers. The increased tactile sensation in both the downward and upward direction of the foot pedal position enabled by the present foot pedal detent assembly represents an improvement in the art.

Figure 6:
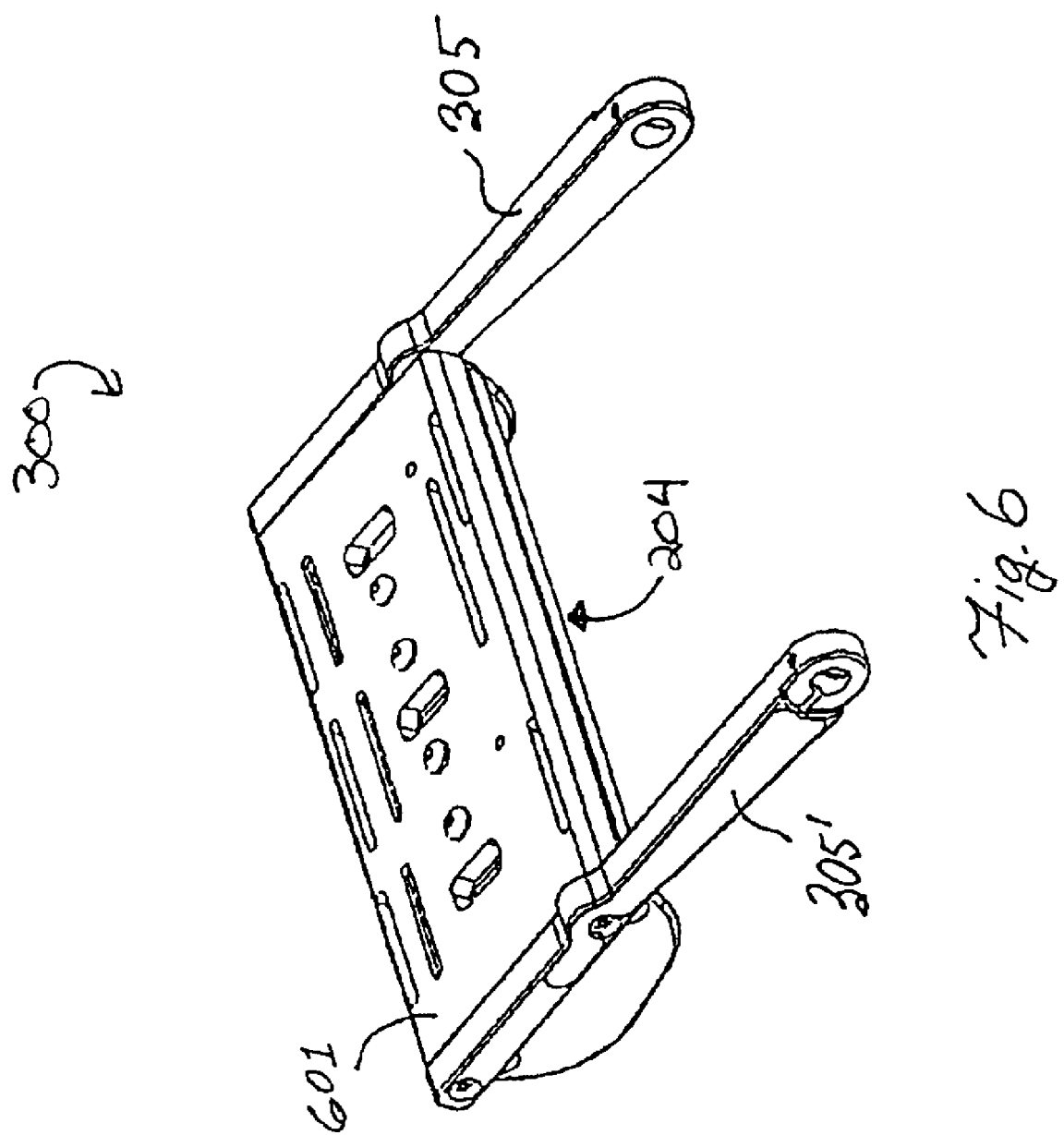
FIG. 6 is a perspective view of a portion of foot pedal assembly showing the bottom of the foot pedal and foot pedal support arms.
Figure 7:
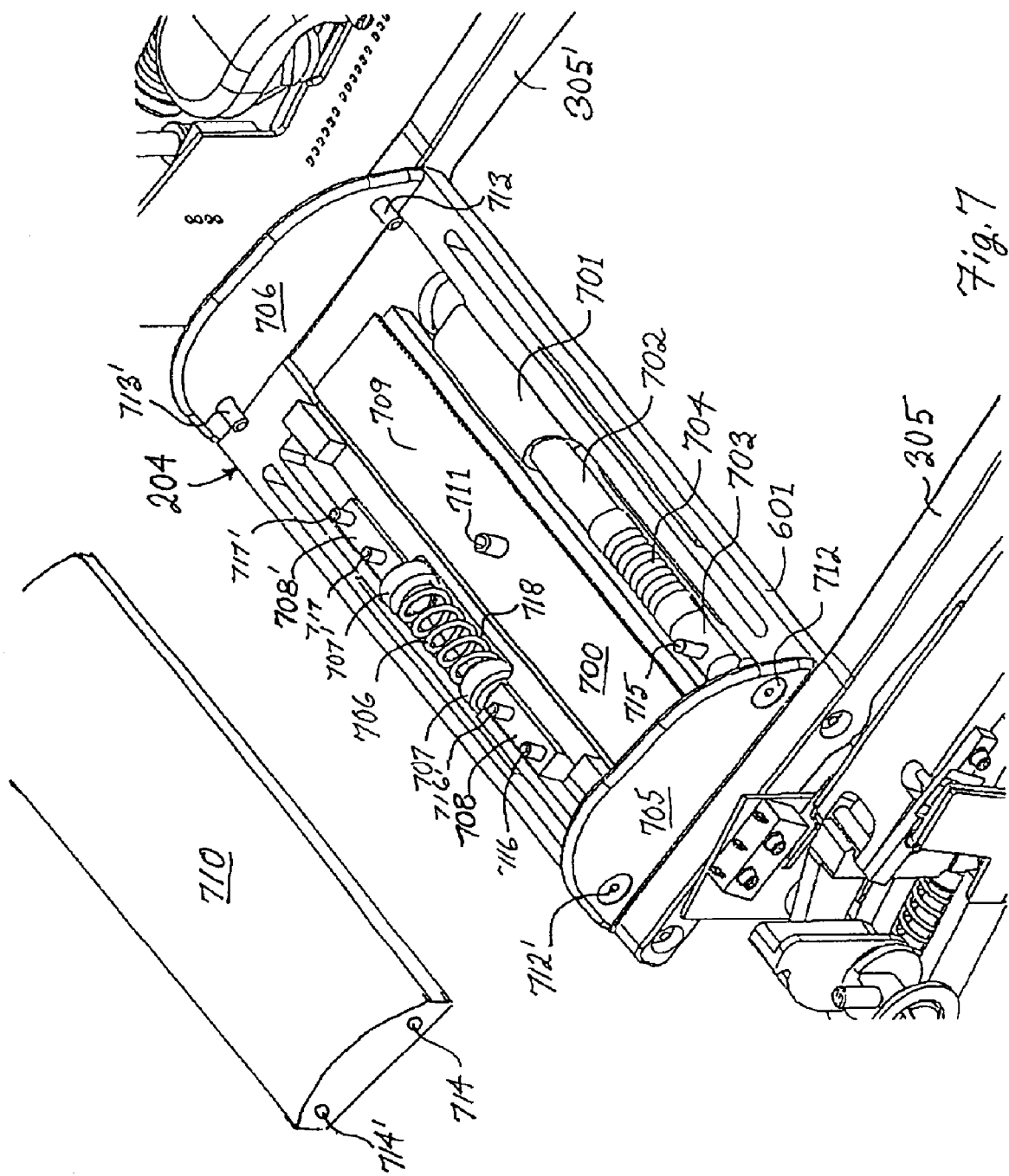
FIG. 7 is a perspective view of the foot pedal assembly with the foot pedal cover removed.

Returning to the foot pedal assembly 300 of the present invention, the foot pedal 204 portion of the foot pedal assembly is shown in bottom perspective view in FIG. 6 and top perspective view in FIG. 7. The foot pedal 204 includes a pedal base 601 rigidly attached to support arms 305 and 305' at the lateral ends thereof. A slider mechanism 700 is rigidly attached to the pedal base 601, as is a linear potentiometer 702. The linear potentiometer 702 has a slidably mounted brush (not shown), disposed therewithin. A potentiometer actuator 703 is attached to the brush such that axial motion of the actuator 703 repositions the brush within the potentiometer thereby changing the output signal from the potentiometer. An axially compressible bellows 704 overlies the brush and protects the brush 702 from contamination by particulates, fluids and the like. The foot pedal cover 710, which includes a left side plate 705 and right side plate 706, is rigidly attached to the slider mechanism 700 and is coupled to potentiometer actuator 704 through post 715.

FIG. 7 shows the foot pedal 204 with the foot pedal cover 710 removed to expose the functional elements of the foot pedal. The foot pedal 204 includes a 2-piece ball-bearing slider mechanism 700. The lower, stationary section (not visible in FIG. 7) of the slider mechanism 700 is rigidly mounted to base 601 from below. The slidably mounted upper section 709 is captured by the lower section along the two ball-bearing edges of the slider mechanism 700 and slides reciprocally back and forth on the lower section. The foot pedal cover 710 is rigidly mounted to the upper section 709 of the slider mechanism 700 by attachment means 711. The left and right side push plates 705 and 706 are rigidly attached to the foot pedal cover 710 by screws 712, 712', and 713, 713', respectively. Screws 712 and 712' insert into holes 714 and 714' respectively on foot pedal cover 710.

Foot pedal cover centering guides 708 and 708' are rigidly mounted to the underside of the foot pedal cover 710 by means of four screws 716, 716' and 717, 717' respectively. A foot pedal cover centering spring 706 and spring caps 707 and 707' are disposed within a recessed space in the base 601 and are captured when the foot pedal cover is attached to the foot pedal. Post 715 is rigidly mounted to the underside of the foot pedal cover 710 and, when the foot pedal cover 710 is positioned over the foot pedal assembly 204, inserts into a hole in the head of a potentiometer brush driving assembly comprised collectively of elements 703 and 704 which provide a connection between the foot pedal cover 710 and the brush of the linear potentiometer 702. The portion of the linear potentiometer 702, exclusive of the brush assembly, is rigidly affixed to the base 601 by attachment means such as, for example, an adhesive. The brush assembly 703 and 704 of the potentiometer includes a plunger shaft (hidden by bellows 704) that extends into the body of the potentiometer 702. As the foot pedal cover 710 is moved laterally back and forth in relation to the base 601, the post 715 forces the plunger shaft of the potentiometer brush assembly to move in and out of the body of the potentiometer 702. This causes a variable electrical output signal to be sent to the controller unit 101 which may be used to control an instrument.

When the foot pedal cover 710 is moved to the right in relation to the base 601, the foot pedal cover centering guide 708 pushes against spring cap 707 and compresses spring 706 against the right edge of the base recess 718 that contains the spring 706 and spring caps 707 and 707'. When the force that is propelling the foot pedal cover to the right is released, the spring 706 rebounds to recenter the foot pedal cover 710. When the foot pedal cover is moved to the left in relation to the base 601, the foot pedal cover centering guide 708' pushes against spring cap 707' and compresses spring 706 against the left edge of the base recess 718 that contains the spring and spring caps. When the force that is moving the foot switch pedal cover to the left is released, the spring 706 rebounds to recenter the foot switch pedal cover with respect to the base 601.

Figure 8:
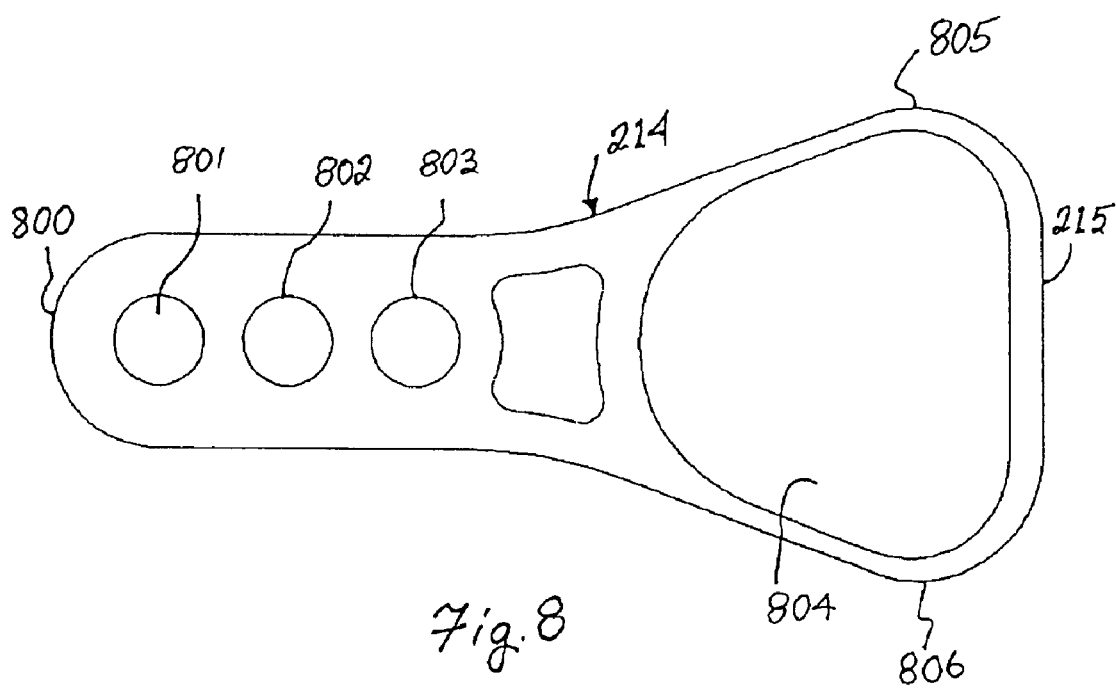
FIG. 8 is a top view of a foot pad.
Figure 9:
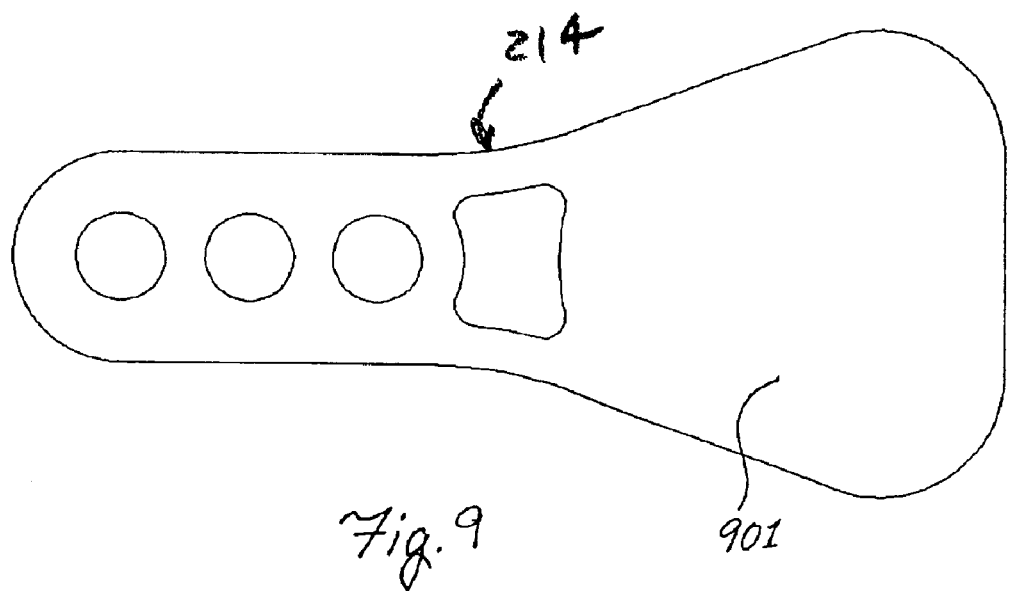
FIG. 9 is a bottom view of a foot pad.

A foot pad 214 (shown in FIGS. 2, 8 and 9) is interposed between an operator's foot and the foot pedal cover 710 which provides a surface dimensioned to receive the sole of an operator's foot. The proximal end 800 of the foot pad is rotatably captured by the heel plate 205 of the controller 110 by one of three circular cutouts 801, 802 or 803, the choice of cutout depending on the size of the operator's foot. A portion 804 of the upper surface of the foot pad, shown in FIG. 8, includes a non-slip surface that provides intimate contact with the sole of the operator's foot. The distal end 215 of the foot pad 214 slides back and forth on top of the foot pedal cover 710. The left and right edges, 805 and 806 respectively, of the foot pad, when rotated, push against the side push plates 705 and 706 of the foot pedal. The greatest width of the foot pad 214 is less than the spacing between the side push plates 705 and 706. The foot pad 214 presents a low-friction surface 901 on the lower surface thereof, as illustrated in FIG. 9, which enables substantially resistance-free motion of the foot pad over the foot pedal cover between the side push plates. Thus, an operator is able to rotate the foot pad either clockwise or counterclockwise from a centrally disposed neutral position with little resistance until an edge of the foot pad encounters one of the side plates 705 or 706 and encounters a resistive barrier opposing further rotation. When such an encounter between the edge of the foot pad and a side plate occurs during foot rotation, the operator is able to sense the change in mechanical resistance and is immediately alerted to the initiation of an event wherein continued rotation of the operator's foot with increased force will result in changing the control signal provided by the potentiometer. This ability to rotate the foot pad without affecting a control signal until a resistance is felt by the operator enables the operator move their foot slightly without changing any of the functions controlled by the foot pedal, allowing the operator to seek a comfortable position during a lengthy procedure without affecting the procedure.

When the foot pedal cover 710 is centered (i.e., neither edge of the foot pad has displaced the foot pedal cover and the spring 706 is not compressed), the output control signal from the potentiometer is at 50% of its maximum output value. Accordingly, when the foot pedal cover moves the potentiometer brush to its right or left limit, the output control signal from the potentiometer will vary between 0 and 100% of its maximum value. The control signal output from the potentiometer can be interpreted by a trigger circuit or microprocessor means to be either an on/off command or a linear output signal, the magnitude of which linear output signal being proportional to the position of the brush within the body of the potentiometer. Such a microprocessor may be programmable and disposed on the foot operable controller near the potentiometer as, for example, on the right pedal suspension arm. The output from the trigger circuit or microprocessor may then be communicated to the control unit 101 by suitable conduction means such as a cable, thereafter to control an operative function.

In summary, in addition to the aforesaid advantages related to vertical displacement of the foot pedal, the foot operable controller of the present invention is operable for enabling an operator to control an instrument by lateral rotation of the operator's foot supported by a slidable pedal cover having, in a preferred embodiment, spring-loaded left and right push plates on lateral edges thereof. The left and right push plates are spaced a first distance from one another to accommodate the greatest width of a foot pad therebetween. The foot pedal includes a control signal generating device such as a linear potentiometer wherein the control signal generating device produces a measurable control signal having a magnitude responsive and/or proportional to lateral movement of the foot pedal cover in a plane substantially parallel to the plane occupied by the controller base.

The foot pad, which is disposed between the operator's foot and the foot pedal cover, is preferably a planar sheet of a suitable material such as plastic having a length, a distal end having a greatest width and a proximal end rotatably captured by a heel plate disposed on the controller base. The foot pad is shaped and dimensioned to accommodate the sole of an operator's foot placed thereon. The distal end of the foot pad having the greatest width overlies a portion of the foot pedal cover such that the greatest width of the foot pad is disposed between the left and right push plates and wherein the greatest width of the foot pad is less than the distance between the push plates. The foot pad is freely rotatable in the region of the foot pedal cover between the push plates. This feature enables the operator to detect, via a change in rotational resistance, when further rotation of the foot pad will cause a change in the control signal. Resistance to counterclockwise or clockwise rotation of the foot pad in the region of the foot pedal between the left and right push plates is less than the resistance to counterclockwise or clockwise rotation that is encountered when the left or right edge of the foot pad is in contact with the left or right push plates respectively.

Figure 10:
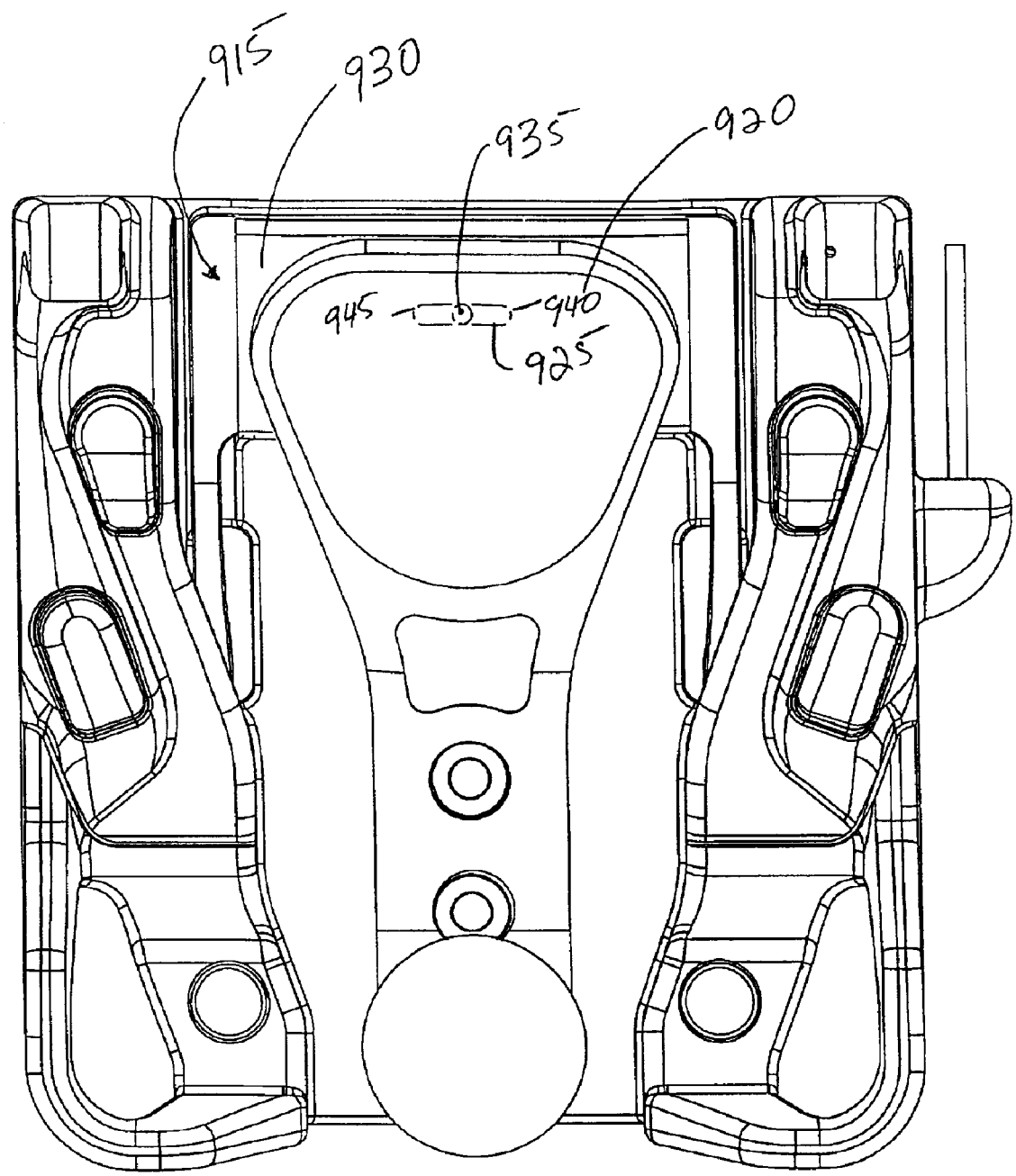
FIG. 10 is a top view of another embodiment of a foot pad showing a slot for engaging a post in mechanical communication with a signal generator.

In an alternate embodiment, as depicted in FIG. 10, a foot pedal assembly 915 includes a foot pad 920 having slot 925 located in a distal end of the foot pad is interposed between an operator's foot and a foot pedal cover 930 in mechanical communication with a signal generator (not shown). A post coupled to the foot pedal cover 930 extends through the slot 925. The slot has right and left lateral ends 940, 945. The length of the slot, that is, the distance between the right and left lateral ends 940, 945 of the slot, provide a neutral zone in which the foot pad may be moved without the right and left lateral ends engaging the post 935. This construction provides for movement of the foot pad through a selected distance about the post without communicating any of the foot pad movement to the post 935, and thence to the foot pedal cover 930 and the signal generator, thus allowing some lateral or azimuthal movement of the foot pad 920 without activating or changing any of the functions of an instrument being controlled by the foot pedal. Alternatively, the foot pedal cover 930 may be eliminated, and the post 935 may be in mechanical communication with the signal generator.

While particular embodiments of the present invention have been illustrated and described, it will be apparent that various modifications can be made without departing from the spirit and scope of the invention. Accordingly, it is not intended that the invention be limited, except as by the appended claims.

We claim:

1. A foot operable controller operable for enabling an operator to control an instrument comprising: a floor-supportable controller base having a lower surface, an upper surface defining a first plane and left and right sides; a foot pedal assembly having a foot pedal affixed to a shaft, said shaft being rotatably mounted on said upper surface of said controller base; a detent assembly mounted on said controller base, said detent assembly being responsive to rotation of said shaft and providing means for exerting a tactilely perceptive change in resistance to rotation of said shaft when said shaft rotationally traverses a predetermined rotational position.

2. The foot operable controller of claim 1, further comprising a control signal generating device, said control signal having a measurable variable property associated therewith, said variable property having a value which varies in response to rotation of said shaft, and wherein the value of said control signal is communicated to the instrument.

3. The foot operable controller of claim 2, wherein said control signal generating device is a potentiometer.

4. The foot operable controller of claim 2, wherein said control signal generating device is an optical shaft position encoder.

5. The foot operable controller of claim 1, wherein said detent assembly comprises a detent base, a detent arm having a proximal end affixed to said shaft and a distal end in opposition to said proximal end, the detent arm rotating in response to rotation of said shaft, a spring disposed between said pivotally mounted detent arm and said base, and a cam carriage slidably mounted on said base and operably engaged with said detent arm to provide variable resistance to said shaft rotation.

6. The foot operable controller of claim 5, wherein said detent assembly further comprises cam carriage disengagement means operable for reversibly disengaging said detent arm from said cam carriage.

7. A foot operable controller operable for enabling an operator to control an instrument comprising: a foot pedal assembly having a foot pedal, said foot pedal being laterally and vertically displaceable from a rest position; and an output signal generator in operable communication with the foot pedal, the output signal generator providing an instrument control signal having a value responsive to displacement of said foot pedal, wherein said foot pedal is laterally displaceable over a distance centered on said rest position.

8. The foot operable controller of claim 7, wherein displacement of said footswitch pedal within a portion of said distance adjacent to said rest position does not change the value of the control signal.

9. The foot operable controller of claim 7, wherein the foot pedal assembly is mounted on a controller base and further comprising a heel plate rotatably mounted on the controller base such that the heel plate cooperates with the foot pedal assembly to provide for lateral movement of an operator's foot without displacing the foot pedal.

10. A foot operable controller operable for enabling an operator to control an instrument comprising: a floor-supportable controller base having a lower surface, an upper surface defining a first plane and left and right sides; a foot pedal assembly mounted on said upper surface of said base, said foot pedal assembly having a foot pedal having a foot pedal base and a foot pedal cover moveably mounted thereon, and a control signal generating device operably attached to the foot pedal cover, the control signal generating device producing a measurable control signal having a magnitude responsive to lateral movement of said foot pedal cover relative to the foot pedal base in a plane substantially parallel to said first plane.

11. The foot operable controller of claim 10, the foot pedal cover further comprising: left and right resistance means mounted on lateral edges of the slidable foot pedal cover, said left and right resistance means being spaced a first distance from one another.

12. The foot operable controller of claim 11, further comprising: a foot pad having a length and a distal end with a greatest width less than said first distance and a proximal end rotatably attached to said controller base, said distal end of the foot pad overlying a portion of said foot pedal cover, said greatest width of the distal end being disposed between said left and right resistance means.

13. The foot operable controller in accordance with claim 12, wherein resistance to substantially lateral movement of said foot pad between said left and right resistance means is less than resistance to substantially lateral movement of the foot pad when a left or right edge of the foot pad is in contact with said left or right resistance means respectively.

14. The foot operable controller of claim 11, further comprising: a foot pad having a length and a proximal end and a distal end, the proximal end rotatably mounted on said controller base, the distal end overlying a portion of the foot pedal cover and disposed between the left and right resistance means and movable therebetween.

15. The foot operable controller of claim 11, wherein said left and right resistance means comprise spring-loaded push plates.

16. The foot operable controller of claim 10, further comprising a heel plate rotatably mounted on said controller base.

17. A foot operable controller for enabling an operator to control a surgical instrument by moving a foot pedal through a vertical distance by application of force thereto, the vertical distance being partitioned into at least two discrete segments with a transition zone located between each of the adjacent segments, each of said segments corresponding to one of a plurality of instrument control settings, and wherein the force required to move the foot pedal through at least one of the segments over a portion of the at least one of the segments and increases over a following portion of the at least one of the segments.

18. A foot operable controller operable for enabling an operator to control a surgical instrument by moving a foot pedal wherein the foot pedal is movable through a distance by changing a force applied to the foot pedal, said distance being partitioned into discrete segments having transition zones therebetween, each of said discrete segments corresponding to one of a plurality of instrument control signals, and wherein the force required to move said foot pedal through a distance coextensive with at least one of said discrete segments decreases over a portion of the at least one of the discrete segments and increases over another portion of the at least one of the discrete segments.

19. The foot operable controller of claim 18, wherein said decrease in force is at least fifteen percent less than the force applied to the foot pedal when the foot pedal is at a transition zone bounding the at least one of the discrete segments.

20. The foot operable controller of claim 18 wherein said decrease in force is at least thirty percent less than the force applied to the foot-switch pedal when the foot pedal is at a transition zone bounding the at least one of the discrete segments.

21. The foot operable controller of claim 18, wherein when said foot pedal is positioned within one of the discrete segments, the force applied to the foot pedal increases when the foot pedal approaches a transition zone bounding the discrete segment.

22. The foot operable controller of claim 21, wherein when said discrete segment includes a position therewithin wherein the force applied to the foot pedal is a minimum value and wherein the force applied to the foot pedal is fifteen percent greater than said minimum value when said foot pedal is positioned at a transition zone bounding the discrete segment.

23. The foot operable controller of claim 21, wherein when said discrete segment includes a position therewithin wherein the force applied to said foot pedal is a minimum value and wherein the force applied to the foot pedal is thirty percent greater than said minimum value when the foot pedal is positioned at a transition zone bounding the discrete segment.

24. The foot operable controller of claim 18, further comprising a detent assembly in mechanical communication with the foot pedal, said detent assembly providing means for changing the force required to move said foot pedal through a distance coextensive with one of the discrete segments.

25. The foot operable controller of claim 24, wherein said detent assembly comprises a spring-loaded cam and cam roller.

26. The foot operable controller of claim 24, further comprising cam disengagement means operable for disengaging said detent assembly from mechanical communication with the foot pedal.

27. The foot operable controller of claim 18, wherein the surgical instrument is an ophthalmic surgical instrument.

28. A foot operable controller for enabling an operator to generate a control signal for controlling a surgical instrument, comprising: a foot pedal movable in both a vertical direction and a horizontal direction by increasing or decreasing a force applied to the foot pedal in said respective vertical and horizontal directions; and a control signal generator in operable communication with the foot pedal and responsive to movement of the foot pedal in the vertical and horizontal directions to generate control signals for controlling a surgical instrument,
 wherein said foot pedal is movable through a horizontal distance in a horizontal direction, a portion of said horizontal distance being a neutral zone wherein application of a minimum, substantially constant force in a horizontal direction moves said foot pedal within said neutral zone.

29. The foot operable controller of claim 28, wherein movement of said foot pedal within said neutral zone does not change said control signal.

30. The foot operable controller of claim 29, wherein said neutral zone is bounded by a resistive barrier to horizontal movement of said foot pedal from said neutral zone to portions of said horizontal distance outside said neutral zone.

31. The foot operable controller of claim 30 wherein horizontal movement of the foot pedal from said neutral zone to a portion of said horizontal distance outside of said neutral zone provides a control signal operable for controlling a function of the surgical instrument.

32. The foot operable controller of claim 30 wherein the force required to move the foot pedal across said resistive barrier is at least fifteen percent greater than said minimum, substantially constant force.

33. The foot operable controller of claim 28, wherein the foot pedal is mounted on a controller base and further comprising a heel plate rotatably mounted on the controller base such that the heel plate cooperates with the foot pedal assembly to provide for lateral movement of an operator's foot without moving the foot pedal.

34. A foot operable controller, comprising: a floor-supportable controller base having a lower surface, an upper surface defining a first plane and left and right sides; a foot pedal assembly having a foot pedal affixed to a shaft, said shaft being rotatably mounted on said upper surface of said controller base; a detent assembly mounted on said controller base, said detent assembly being responsive to rotation of said shaft and providing means for exerting a tactilely perceptive change in resistance to rotation of said shaft when said shaft rotationally traverses a predetermined rotational position, the detent assembly having a detent base, a detent arm having a proximal end affixed to said shaft and a distal end in opposition to said proximal end, the detent arm rotating in response to rotation of said shaft, a spring disposed between said pivotally mounted detent arm and said base, and a cam carriage slidably mounted on said base and operably engaged with said detent arm to provide variable resistance to said shaft rotation.

35. The foot operable controller of claim 34, wherein said detent assembly further comprises cam carriage disengagement means operable for reversibly disengaging said detent arm from said cam carriage.

36. A foot operable controller, comprising: a floor-supportable controller base having a lower surface, an upper surface defining a first plane and left and right sides; a foot pedal assembly having a foot pedal affixed to a shaft, said shaft being rotatably mounted on said upper surface of said controller base; a detent assembly mounted on said controller base, said detent assembly being responsive to rotation of said shaft and providing means for exerting a tactilely perceptive change in resistance to rotation of said shaft when said shaft rotationally traverses a predetermined rotational position, the detent assembly having a detent base, a detent arm having a proximal end affixed to said shaft and a distal end in opposition to said proximal end, the detent arm rotating in response to rotation of said shaft, a spring disposed between said pivotally mounted detent arm and said base, and a cam carriage slidably mounted on said base and operably engaged with said detent arm to provide variable resistance to said shaft rotation; and a control signal generating device in operable communication with said shaft, said control signal having a measurable variable property associated therewith, said variable property having a value which varies in response to rotation of said shaft, and wherein the value of said control signal is communicated to an instrument to be controlled.

37. The foot operable controller of claim 36, wherein said control signal generating device is a potentiometer.

38. The foot operable controller of claim 36, wherein said control signal generating device is an optical shaft position encoder.

39. The foot operable controller of claim 36, wherein said detent assembly further comprises cam carriage disengagement means operable for reversibly disengaging said detent arm from said cam carriage.

40. A foot operable controller operable for enabling an operator to control an instrument comprising: a floor-supportable controller base having a lower surface, an upper surface defining a first plane and left and right sides; a foot pedal assembly mounted on said upper surface of said base, said foot pedal assembly having a foot pedal base mounted on said upper surface of said base, a control signal generating device mounted on said foot pedal base, and left and right resistance means in mechanical communication with the control signal generating device, the left and right resistance means separated by a distance defining a neutral zone and configured to be engaged by lateral movement of an operator's foot, the neutral zone allowing movement of the operator's foot through the neutral zone without communicating the movement of the operator's foot to the control signal generating device, the control signal generating device producing a measurable control signal having a magnitude responsive to lateral movement of the operator's foot relative to the foot pedal base when the movement of the operator's foot engages the left or right resistance means.

41. The foot operable controller of claim 40, wherein the foot pedal further comprises: a foot pedal cover slidably mounted on the foot pedal base and coupled to the control signal generating device; wherein the left and right resistance means are mounted on lateral edges of the foot pedal cover.

42. The foot operable controller of claim 41, further comprising: a foot pad having a length and a proximal end and a distal end, the proximal end rotatably mounted on said controller base, the distal end overlying a portion of the foot pedal cover and disposed between the left and right resistance means and movable therebetween.

43. The foot operable controller of claim 41, wherein said left and right resistance means comprise spring-loaded push plates.

44. The foot operable controller of claim 40, further comprising: a foot pad having a length and a distal end with a greatest width less than said neutral zone and a proximal end rotatably attached to said controller base, said distal end of the foot pad overlying a portion of said foot pedal base, said greatest width of the distal end being disposed between said left and right resistance means.

45. The foot operable controller in accordance with claim 44, wherein resistance to substantially lateral movement of said foot pad between said left and right resistance means is less than resistance to substantially lateral movement of the foot pad when a left or right edge of the foot pad is in contact with said left or right resistance means respectively.

46. The foot operable controller of claim 40, wherein the left and right resistance means comprise right and left lateral ends of a slot formed in a distal end of a foot pad also having a proximal end rotatably mounted to said upper surface of said base, and the foot pad is mechanically coupled to the control signal generating device by a post in mechanical communication with the control signal generating device extending through the slot such that the foot pad is free to move laterally about the post without engaging the post until the right or left lateral ends of the slot engage the post, thereby communicating further lateral movement in the same direction to the control signal generating device.

47. The foot operable controller of claim 40, further comprising a heel plate rotatably mounted on the controller base such that the heel plate cooperates with the foot pedal assembly to provide for movement of an operator's foot without communicating the movement of the operator's foot to the control signal generating device.

48. A foot operable controller operable for enabling an operator to control an instrument comprising: a floor-supportable controller base having a lower surface, an upper surface defining a first plane and left and right sides; a foot pedal assembly mounted on said upper surface of said base, said foot pedal assembly having a foot pedal base pivotally mounted on said upper surface of said base, the pivotal mounting providing for vertical movement of the foot pedal base in relation to the upper surface of said base, a control signal generating device mounted on said foot pedal base, and left and right resistance means in mechanical communication with the control signal generating device, the left and right resistance means separated by a distance defining a neutral zone and configured to be engaged by lateral movement of an operator's foot, the neutral zone allowing movement of the operator's foot through the neutral zone without communicating the movement of the operator's foot to the control signal generating device, the control signal generating device producing a measurable control signal having a magnitude responsive to lateral movement of the operator's foot relative to the foot pedal base when the movement of the operator's foot engages the left or right resistance means.

49. The foot operable controller of claim 48, wherein the foot pedal base is in mechanical communication with a shaft, said shaft being rotatably mounted on said upper surface of said controller base and wherein the foot pedal assembly further comprises: a detent assembly mounted on said controller base, said detent assembly being responsive to rotation of said shaft and providing means for exerting a tactilely perceptive change in resistance to rotation of said shaft when said shaft rotationally traverses a predetermined rotational position, the detent assembly having a detent base, a detent arm having a proximal end affixed to said shaft and a distal end in opposition to said proximal end, the detent arm rotating in response to rotation of said shaft, a spring disposed between said pivotally mounted detent arm and said base, and a cam carriage slidably mounted on said base and operably engaged with said detent arm to provide variable resistance to said shaft rotation; and a second control signal generating device in operable communication with said shaft for generating a second control signal, said second control signal having a measurable variable property associated therewith, said variable property having a value which varies in response to rotation of said shaft, and wherein the value of said second control signal is communicated to an instrument to be controlled.

50. A foot operable controller operable for enabling an operator to control an instrument comprising: a floor-supportable controller base having a lower surface, an upper surface defining a first plane and left and right sides; a foot pedal assembly mounted on said upper surface of said base, said foot pedal assembly having a foot pedal base in mechanical communication with shaft, said shaft being rotatably mounted on said upper surface of said controller base, the rotation of the shaft providing for vertical movement of the foot pedal base in relation to the upper surface of said base, a control signal generating device mounted on said foot pedal base, left and right resistance means in mechanical communication with the control signal generating device, the left and right resistance means separated by a distance defining a neutral zone and configured to be engaged by lateral movement of an operator's foot, the neutral zone allowing movement of the operator's foot through the neutral zone without communicating the movement of the operator's foot to the control signal generating device, the control signal generating device producing a measurable control signal having a magnitude responsive to movement of the operator's foot relative to the foot pedal base when the movement of the operator's foot engages the left or right resistance means; and a detent assembly mounted on said controller base, said detent assembly being responsive to rotation of said shaft and providing means for exerting a tactilely perceptive change in resistance to rotation of said shaft when said shaft rotationally traverses a predetermined rotational position.

51. The foot operable controller of claim 50, wherein the detent assembly includes a detent base; a detent arm having a proximal end affixed to said shaft and a distal end in opposition to said proximal end, the detent arm rotating in response to rotation of said shaft; a spring disposed between said pivotally mounted detent arm and said base; a cam carriage slidably mounted on said base and operably engaged with said detent arm to provide variable resistance to said shaft rotation; and a second control signal generating device in operable communication with said shaft for generating a second control signal, said second control signal having a measurable variable property associated therewith, said variable property having a value which varies in response to rotation of said shaft, and wherein the value of said second control signal is communicated to an instrument to be controlled.

52. A method for providing tactile feedback to an operator of a foot pedal as the foot pedal is displaced in a downward direction to control one or more functions of an instrument to signal the operator that a selected function of the instrument is about to be engaged, comprising: providing a first tactilely perceivable resistance as a foot pedal is depressed through a selected vertical distance; providing a second tactilely perceivable resistance as the foot pedal is further depressed beyond the selected vertical distance, the second tactilely perceivable resistance being less than the first tactilely perceivable resistance.

53. The method of claim 52, wherein the second tactilely perceivable resistance is provided for a second selected vertical distance and further comprising providing a third tactilely perceivable resistance as the foot pedal is further depressed beyond the second selected vertical distance, the third tactilely perceivable resistance being greater than the second tactilely perceivable resistance.

54. A method for providing tactile feedback to an operator of a foot pedal as the foot pedal is moved in a vertical direction to control an instrument to signal the operator that a selected function of the instrument is about to be engaged, comprising: providing a first tactilely perceivable resistance as the foot pedal is moved over a first vertical distance; providing a second tactilely perceivable resistance as the foot pedal is moved a second vertical distance, the second tactilely perceivable resistance being less than the first tactilely perceivable resistance; and providing a third tactilely perceivable resistance as the foot pedal is moved a third vertical distance, the third tactilely perceivable resistance being greater than the second tactilely perceivable resistance.

* * * * *

UNITED STATES PATENT AND TRADEMARK OFFICE
CERTIFICATE OF CORRECTION

PATENT NO. : 7,012,203 B2 Page 1 of 1
APPLICATION NO. : 09/949123
DATED : March 14, 2006
INVENTOR(S) : Michael R. Hanson et al.

It is certified that error appears in the above-identified patent and that said Letters Patent is hereby corrected as shown below:

In Summary of the Invention (column 3, line 46), change "surgeons foot" to --surgeon's foot--

In Summary of the Invention (column 4, line 40), change "support arms," to --support arms.--

In Description of the Preferred Embodiments (column 10, line 33), change "A similar change is" to --A similar change in--

Signed and Sealed this

Fifteenth Day of August, 2006

JON W. DUDAS
*Director of the United States Patent and Trademark Office*